United States Patent [19]

Fujii et al.

[11] 4,021,472

[45] May 3, 1977

[54] GUANIDINOBENZOIC ACID DERIVATIVES

[75] Inventors: Setsuro Fujii, Tokushima; Yoshiaki Uegai, Ibaraki; Tsuyoshi Watanabe, Kadoma; Naohiro Kayama, Takatsuki, all of Japan

[73] Assignee: Ono Pharmaceutical Co., Ltd., Osaka, Japan

[22] Filed: Nov. 3, 1975

[21] Appl. No.: 628,676

[30] Foreign Application Priority Data

Nov. 1, 1974 Japan .............................. 49-125499
Dec. 17, 1974 Japan .............................. 49-144103
May 27, 1975 Japan .............................. 50-62519

[52] U.S. Cl. .......................... 260/472; 260/473 S; 424/310
[51] Int. Cl.² ..................................... C07C 129/12
[58] Field of Search ...................... 260/471 R, 472

[56] References Cited

FOREIGN PATENTS OR APPLICATIONS 70,574 1/1970 Germany ...................... 260/471 R

*Primary Examiner*—Jane S. Myers
*Attorney, Agent, or Firm*—Sughrue, Rothwell, Mion, Zinn & Macpeak

[57] ABSTRACT

Guanidinobenzoic acid derivatives represented by formula (I)

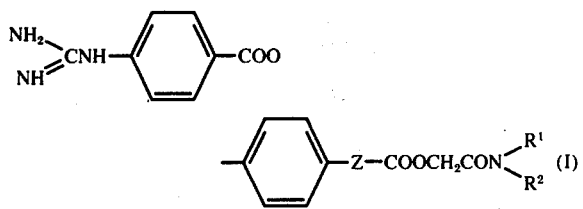

wherein $R^1$, $R^2$ and $Z$ are as defined hereinafter, having anti-plasmin and anti-trypsin activities, intermediates useful for the synthesis thereof and processes for preparing the same.

6 Claims, No Drawings

GUANIDINOBENZOIC ACID DERIVATIVES

BACKGROUND OF THE INVENTION

1. Field of the Invention

This invention relates to novel guanidinobenzoic acid derivatives, novel intermediates useful for the synthesis of the guanidinobenzoic acid derivatives and processes of producing the guanidinobenzoic acid derivatives and the intermediates therefor.

2. Description of the Prior Art

The following compounds are known to have anti-plasmin and anti-trypsin activities.

Anti-plasmin agent: trans-4-aminomethylcyclohexanecarboxylic acid as disclosed in S. Okamoto and U. Okamoto, Keio Journal of Medicine, 11, 105 (1962), Anti-trypsin agent: "Trasylol" as described in B. Kassel et al, J. Biol. Chem., 238, 3274 (1963).

However, these known anti-plasmin and anti-trypsin agents are disadvantageous in that they exhibit relatively low activities and low water-solubility.

The compounds represented by formula (I) possess extremely potent activities as compared with those of the above anti-plasmin and anti-trypsin agents, thereby making it possible to attain the same effect at a lower dosage level upon administration of the compounds of formula (I). Also, the compounds of formula (I) have a water-solubility sufficient to permit administration of these compounds in the form of aqueous solutions.

SUMMARY OF THE INVENTION

An object of this invention is, therefore, to provide compounds represented by formula (I) which is useful as a pharmaceutical.

Another object of this invention is to provide guanidinobenzoic acid compounds of excellent solubility in solvents or solutions as are commonly employed in pharmaceutical preparations such as water, physiological salt solutions and the like.

Still another object of this invention is to provide guanidinobenzoic acid compounds of high potency with respect to the above-described pharmacological activities at low dose levels, and to provide a process for preparing such compounds.

A further object of this invention is to provide an intermediate for the synthesis of the above-described guanidinobenzoic acid compound, and a process for preparing the intermediate.

As a result of extensive research on anti-plasmin and anti-trypsin agents, we have found that a series of compounds represented by formula (I) above have antiplasmin and anti-trypsin activities, and show excellent solubility.

This invention thus relates to novel guanidinobenzoic acid derivatives represented by formula (I)

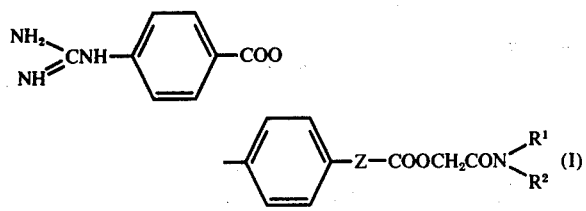

wherein $R^1$ and $R^2$, which may be the same or different, each represents a hydrogen atom or a lower alkyl group having 1 to 3 carbon atoms; and Z represents a carbon-to-carbon covalent bond, a methylene group, an ethylene group, or a vinylene group; to the acid addition salts of the above guanidinobenzoic acid derivatives, novel intermediates useful for the preparation of the compounds of formula (I), processes for preparing compounds of formula (I) and processes for preparing the intermediates useful for preparing the compounds of formula (I).

DETAILED DESCRIPTION OF THE INVENTION

The term "lower alkyl" as is used throughout the specification and claims means a straight or branched chain alkyl group having 1 to 3 carbon atoms including methyl, ethyl, n-propyl and isopropyl groups.

The novel guanidinobenzoic acid derivatives and the novel intermediates therefor can be prepared according to the following reaction scheme:

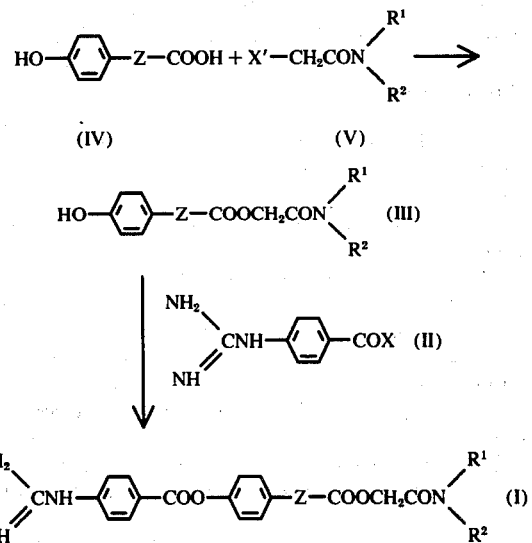

wherein $R^1$, $R^2$ and Z are as defined above, and X and X' each represents a halogen atom such as a fluorine, chlorine, bromine or iodine atom.

The compound of formula (I) can be prepared by reacting a p-guanidinobenzoyl halide represented by formula (II) with a compound represented by formula (III) in the presence of a dehydrohalogenating agent.

The p-guanidinobenzoyl halide of formula (II) which can be used as a starting material in the present invention is easily obtained from p-guanidinobenzoic acid in a conventional manner. Taking a simple example, p-guanidinobenzoic acid is heated with thionyl chloride to obtain p-guanidinobenzoyl chloride hydrochloride of formula (II), which can be used as it is in this invention (see German Pat. No. 950,637).

The starting compound of formula (III) which can be used in this invention can be prepared by reacting a compound represented by formula (IV) with a compound represented by formula (V) [molar ratio of compound (IV) to compound (V) is about 0.8 to about 1.2] by heating at a temperature of from about 60° to 150° C for about 2 to 20 hours in a solvent such as acetonitrile, tetrahydrofuran, benzene, toluene, dimethylformamide and the like [about 500 to about 2000% v/w based on compound (IV)], in the presence of an organic base (dehydrohalogenating agent) such as triethylamine and tributylamine [about 6 to about 20% w/w based on compound (IV)] at atmospheric pressure.

The reaction between the compound of formula (II) and the compound of formula (III) can be carried out at atmospheric pressure by dissolving or suspending the compound of formula (III) in an organic solvent inert to the reaction, for example, tetrahydrofuran, diethyl ether, benzene, toluene, pyridine and the like, at a concentration of from about 1 to 10 mole %, and adding about 1 to 15 moles of the compound of formula (II) per mole of the compound of formula (III) to the solution or the suspension. Since the reaction is a condensation reaction which by-produces hydrogen halide, the reaction can be conducted in the presence of an organic amine (dehydrohalogenating agent) such as triethylamine, tributylamine, dimethylaniline, pyridine and the like, except when pyridine is employed as a solvent. It is preferred to use pyridine as a solvent since it serves not only as a solvent but also as a dehydrohalogenating agent. The amount of the organic amine used ranges from about 15 to 500%, preferably 300 to 500% by weight, based on the total weight of the starting compounds.

The reaction proceeds relatively easily, and therefore, can be effected at normal temperature (about 20° to 30° C) or with cooling, generally at from about 0° C to normal temperature, for a period of from about 30 minutes to 3 hours, preferably 1 to 2 hours, while stirring.

The desired compound of formula (I) can be obtained as a salt formed with a hydrogen halide. Isolation of the compound can be carried out either by filtering the crystals precipitated in the reaction mixture and adding the crystals to an aqueous solution of sodium bicarbonate or by adding an aqueous solution of sodium bicarbonate to the reaction mixture, thereby crystallizing the product in the form of a carbonate, followed by filtration. The concentration of the aqueous solution of sodium bicarbonate employed ranges from about 5% by weight to saturation. If desired, the thus obtained carbonate of the compound of formula (I) can be converted into an inorganic acid salt such as a hydrochloride, a sulfate, a phosphate, a hydrobromide, a nitrate or a like salt, or an organic acid salt such as an acetate, a lactate, an oxalate, a maleate, a fumarate, a malate, a tartarate, a citrate, an ascorbate, a benzenesulfonate, a toluenesulfonate (tosylate), a methanesulfonate (mesylate) or a like salt.

These acid salts can be prepared, for example, by suspending a carbonate of the compound of formula (I) in water or an alcohol, preferably methanol or ethanol, adding the above acid to the resulting suspension to adjust the pH of the mixture to 1 to 5, preferably 2 to 4, during which time the mixture is warmed, if necessary, at a temperature of 30° to 80° C to obtain a solution, and then cooling the solution to about 5° C or adding a solvent such as diethyl ether, acetone, tetrahydrofuran, dioxane and the like, followed by cooling to about 5° C to obtain the desired acid addition salt as crystals.

The procedures as set forth above can be effected under atmospheric pressure, unless otherwise indicated.

As earlier described, the N-substituted-carbamoylmethyl-p-(p-guanidinobenzoyloxy)phenylalkanoate derivatives of formula (I) according to the present invention are novel compounds which have never been reported in the literature and which exhibit potent inhibitory activities against proteolytic enzymes such as plasmin and trypsin at extremely low concentrations, as shown in Table 1. Further, they are excellent in solubility and, therefore, are suitable for administration as a pharmaceutical in the form of an aqueous solution, a physiological salt solution or other solutions.

The inhibitory activities of representative compounds of formula (I) against plasmin and trypsin in vitro were determined in a manner similar to the method described by M. Muramatsu et al (*J. Biochemistry* 57, 402 (1965)) for plasmin, and the method described by M. Muramatsu et al (*J. Biochemistry* 58, 214 (1964)) for trypsin, as follows:

1. Plasmin: A system comprising 0.1 ml of human euglobulin (10 fold dilution), 0.1 ml of streptokinase (2000 unit/ml), 0.4 ml of fibrinogen (4% solution), 0.3 ml of a 0.1 M borate saline buffer solution (pH 7.4) and 0.1 ml of a solution of each of the following compounds of formula (I) at various concentrations was allowed to react at a temperature of 37° C for 30 minutes. The concentration at which the test compound exhibited 50% inhibition against plasmin was determined, and the results are shown in Table 1 below. Trans-4-aminomethylcyclohexane carboxylic acid, known as an inhibitor against plasmin, was employed as a control.

2. Trypsin: A system comprising 0.4 ml of trypsin (1.25 μg/ml), 0.5 ml of p-tosylarginine methyl ester (20 mM) in Tris-HCl buffer (pH 8.5) and 0.1 ml of a solution of each of the following compounds of formula (I) at various concentrations was reacted at a temperature of 37° C for 30 minutes. The concentration of each of the test compounds at which the activity of trypsin 0.5 μg to hydrolyze p-tosylarginine methyl ester was 50% inhibited is shown in Table 1 below. As a control, Trasylol (tradename of a peptide extracted from bovine organs having an inhibitory activity against a proteolytic enzyme and manufactured by Bayer A.G.) was used.

| Test Compound No. | Structure |
|---|---|
| 1 | NH$_2$\\CNH—⟨C$_6$H$_4$⟩—COO—⟨C$_6$H$_4$⟩—COOCH$_2$CONH$_2$ . CH$_3$SO$_3$H (NH) |
| 2 | NH$_2$\\CNH—⟨C$_6$H$_4$⟩—COO—⟨C$_6$H$_4$⟩—COOCH$_2$CONHCH$_3$ . CH$_3$SO$_3$H (NH) |

-continued

| Test Compound No. | Structure |
|---|---|
| 3 | $\text{H}_2\text{N}-\text{C}(=\text{NH})-\text{NH}-\text{C}_6\text{H}_4-\text{COO}-\text{C}_6\text{H}_4-\text{COOCH}_2\text{CON}(\text{CH}_3)_2 \cdot \text{CH}_3\text{SO}_3\text{H}$ |
| 4 | $\text{H}_2\text{N}-\text{C}(=\text{NH})-\text{NH}-\text{C}_6\text{H}_4-\text{COO}-\text{C}_6\text{H}_4-\text{COOCH}_2\text{CON}(\text{C}_3\text{H}_7)_2 \cdot \text{CH}_3-\text{C}_6\text{H}_4-\text{SO}_3\text{H}$ |
| 5 | $\text{H}_2\text{N}-\text{C}(=\text{NH})-\text{NH}-\text{C}_6\text{H}_4-\text{COO}-\text{C}_6\text{H}_4-\text{CH}_2\text{COOCH}_2\text{CON}(\text{CH}_3)_2 \cdot \text{CH}_3\text{SO}_3\text{H}$ |
| 6 | $\text{H}_2\text{N}-\text{C}(=\text{NH})-\text{NH}-\text{C}_6\text{H}_4-\text{COO}-\text{C}_6\text{H}_4-\text{CH}=\text{CH}-\text{COOCH}_2\text{CON}(\text{CH}_3)_2 \cdot \text{CH}_3\text{SO}_3\text{H}$ |
| 7 | $\text{H}_2\text{N}-\text{C}(=\text{NH})-\text{NH}-\text{C}_6\text{H}_4-\text{COO}-\text{C}_6\text{H}_4-\text{CH}_2\text{CH}_2\text{COOCH}_2\text{CON}(\text{CH}_3)_2 \cdot \text{CH}_3\text{SO}_3\text{H}$ |
| 8 | $\text{H}_2\text{N}-\text{C}(=\text{NH})-\text{NH}-\text{C}_6\text{H}_4-\text{COO}-\text{C}_6\text{H}_4-\text{CH}_2\text{COOCH}_2\text{CONHCH}_3 \cdot \text{CH}_3\text{SO}_3\text{H}$ |

Table 1

| Test Compound No. | 50% Inhibition Concentration Anti-Trypsin | 50% Inhibition Concentration Anti-Plasmin | Solubility in water |
|---|---|---|---|
| 1 | $3.0 \times 10^{-9}$M | $1.5 \times 10^{-8}$M | 1 mM |
| 2 | $3.5 \times 10^{-9}$M | $1.6 \times 10^{-9}$M | 50 mM |
| 3 | $2.7 \times 10^{-9}$M | $2.0 \times 10^{-9}$M | >20 mM |
| 4 | $1.4 \times 10^{-9}$M | $5.3 \times 10^{-10}$M | 10 mM |
| 5 | $8.5 \times 10^{-9}$M | $3.8 \times 10^{-8}$M | 100 mM |
| 6 | $9.0 \times 10^{-11}$M | $1.95 \times 10^{-8}$M | 10 mM |
| 7 | $5.6 \times 10^{-10}$M | $1.2 \times 10^{-7}$M | 10 mM |
| 8 | $1.2 \times 10^{-8}$M | $1.0 \times 10^{-8}$M | 10 mM |
| (Control) Trans-4-amino-methyl-cyclohexane carboxylic acid | | $3.0 \times 10^{-5}$M | |
| Trasylol | $2.8 \times 10^{-6}$M | | |

INHIBITORY EFFECTS FOR FIBRINOLYSIS OF PLASMIN

Inhibitory effects for fibrinolysis of plasmin were examined according to the method of S. Okamoto and U. Okamoto (Keio Journal of Medicine 11 (No. 3) 105 (1962)).

10 ml of human serum was administered to male rabbits weighing 2.0 to 2.5 Kg through the femoral vein, and after 2 minutes 50,000 units of streptokinase was administered to the rabbits intraveneously to activate plasmin.

Each of the test compounds of the present invention was administered to the rabbits at a dosage level of 5 mg/Kg 5 minutes after the administration of streptokinase. After 15, 30, 60, 90, 120 and 180 minutes, 0.5 ml of blood was drawn from the rabbits, and the blood then incubated at 37° C for 3 hrs. to coagulate the blood. The thus formed blood clots were washed with water and dried. The dry weight of the blood clots was evaluated and compared with the normal value (the value obtained prior to administration of the human serum).

The results obtained are shown in Table 2.

The values in Table 2 were calculated according to the following equation:

$$\text{Value} = \frac{\text{Weight (normal)} - \text{Weight (sample)}}{\text{Weight (normal)}} \times 100$$

Table 2

| | Fibrinolytic Activity in Rabbits | | |
|---|---|---|---|
| | Control | Compound No.2 (5 mg/kg iv) | Compound No.5 (5 mg/kg iv) |
| 15 min. after | 99.8% | 0% | 0% |
| 30 min. after | 93% | 0% | 0% |
| 60 min. after | 82% | 2% | 4% |
| 90 min. after | 68% | 2% | 20% |
| 120 min. after | 74% | 12% | 46% |
| 180 min. after | 50% | 31% | 52% |

From Table 2, it can be seen that in the control group 99.8% of the blood clots were dissolved after 15 minutes, which indicates that plasmin is activated.

Further, 50% fibrinolytic activity was observed even after 180 minutes.

On the contrary, the sample groups in which compound No. 2 and compound No. 5 of the present invention were administered intravenously exhibited a plasmin activity of 0 to 20% for up to 90 minutes after administration, which clearly demonstrates that plasmin activity is inhibited.

EFFECTS ON RAT PANCREATITIS

Male Wistar rats weighing 200 to 250 g were laparotomized under anesthetization with pentobarbital and to the thus laparotomized rats 0.1 ml of a mixture of sodium taurocholate and trypsin was administered through the pancreatic duct to induce pancreatitis.

Mortality rates for up to 48 hrs. after the administration were compared between the groups in which the compounds of the present invention were injected intravenously and the control groups in which a physiological salt solution was injected intravenously. The results are shown in Table 3 below.

Table 3

| Effect on Rat Pancreatitis | | |
|---|---|---|
| Intravenous Injection | Mortality for 48 hrs. | |
| Saline (Control) | 85.7% | (12/14) |
| Compound No.2 1 mg/kg | 85.7 | ( 6/7 ) |
| Compound No.2 2.5 mg/kg | 42.8 | ( 3/7 ) |
| Compound No.2 5.0 mg/kg | 30.0 | ( 3/10) |
| Saline (Control) | 78.9 | (15/19) |
| Compound No.5 1 mg/kg | 64.2 | ( 9/14) |
| Compound No.5 2.5 mg/kg | 50.0 | ( 8/16) |
| Compound No.5 5.0 mg/kg | 44.4 | ( 8/14) |

Comparing the mortality rate of rats 48 hrs. after the induction of pancreatitis, the control groups which received an intravenous injection of a physiological salt solution showed a mortality rate of 85.7%, whereas the sample groups which received an intravenous injection of 2.5 mg/kg and 5.0 mg/kg of Compound No. 2, respectively, showed reduced mortality rates of 42.8% and 30%, respectively. In the test series for Compound No. 5, the control groups (physiological salt solution) showed a mortality rate of 78.9%, whereas the sample groups which received an intravenous injection of 2.5 mg/kg and 5.0 mg/kg of compound No. 5, respectively, showed a reduced mortality rate of 50.0% and 44.4% respectively.

From the above it can be concluded that the compounds of the present invention have excellent effects on pancreatitis.

As is apparent from the above results, the compounds of the present invention are highly inhibitory to plasmin and trypsin and, therefore, are useful as pharmaceuticals, i.e., as an anti-plasmin agent for treating bleeding disorders and the like or as an anti-trypsin agent for treating acute pancreatitis and the like.

The present invention is illustrated in further detail by the following Examples, but it should be understood that they are given for illustrative purposes only and are not to be construed as limiting the invention. Unless otherwise indicated, all parts, percents, ratios and the like are by weight and all operations in the following discussion were conducted at atmospheric pressure.

EXAMPLE 1

Carbamoylmethyl-p-Hydroxybenzoate 10 g of p-hydroxybenzoic acid and 10 g of α-bromoacetamide were dissolved in 150 ml of acetonitrile, and 7 g of triethylamine was added to the solution. The resulting mixture was refluxed for 7 hours followed by concentrating under reduced pressure. Water was then added to the residue to obtain 8.4 g of crystals of the above-titled compound having a melting point of 250°–255° C.

EXAMPLE 2

N,N-Dimethylcarbamoylmethyl-p-Hydroxybenzoate 21 g of p-hydroxybenzoic acid, 18.5 g of N,N-dimethyl-α-chloroacetamide and 15.4 g of triethylamine were added to 200 ml of acetonitrile, and the mixture was refluxed for 6 hours while stirring. The mixture was cooled, and the precipitated crystals were filtered, washed with acetonitrile and dried to obtain 24 g of the above-titled compound having a melting point of 183°–186° C.

EXAMPLE 3

N-Methylcarbamoylmethyl-p-Hydroxybenzoate 40 g of p-hydroxybenzoic acid, 44 g of α-bromo-N-methylacetamide and 30 g of triethylamine were added to 330 ml of acetonitrile. The resulting mixture was allowed to react and worked up as described in Example 1. Recrystallization of the product from water gave 39 g of the above-titled compound having a melting point of 163°–165° C.

EXAMPLE 4

N,N-Di-n-Propylcarbamoylmethyl-p-Hydroxybenzoate 17 g of α-bromo-N,N-di-n-propylacetamide (b.p. 108° C/2 mm Hg) obtained from α-bromoacetyl bromide and dipropylamine, 10.6 g of p-hydroxybenzoic acid and 7.7 g of triethylamine were reacted in 120 ml of acetonitrile and the reaction mixture was worked up as described in Example 1 to obtain 10 g of the above-titled compound having a melting point of 102°–103° C.

EXAMPLE 5

N,N-Dimethylcarbamoylmethyl-p-Hydroxyphenylacetate 11 g of α-bromo-N,N-dimethylacetamide and 10 g of p-hydroxyphenylacetic acid were dissolved in 150 ml of acetonitrile, and 9 g of triethylamine was added to the solution. The resulting mixture was refluxed for 7 hours followed by concentrating under reduced pressure. Water was added to the residue to precipitate crystals, which were then filtered and dried to obtain 9 g of the above-tilted compound having a melting point of 102°–105° C.

EXAMPLE 6

N,N-Dimethylcarbamoylmethyl-p-Hydroxycinnamate 5 g of α-bromo-N,N-dimethylacetamide, 5 g of p-hydroxycinnamic acid and 3.5 g of triethylamine were added to 150 ml of acetonitrile, and the mixture was refluxed for 7 hours while stirring. The reaction mixture was then concentrated to half its original volume, and water was added to the residue to precipitate crystals. The thus precipitated crystals were filtered and dried to obtain 5 g of the above-titled compound having a melting point of 205°–206° C.

EXAMPLE 7

N,N-Dimethylcarbamoylmethyl-p-Hydroxyphenylpropionate 5 g of α-bromo-N,N-dimethylacetamide, 5 g of p-hydroxyphenylpropionic acid and 3.5 g of triethylamine were added to 150 ml of acetonitrile. The resulting mixture was reacted and worked up as described in Example 2 to obtain 6 go of the above-titled compound having a melting point of 110°–112° C.

EXAMPLE 8

N-Methylcarbamoylmethyl-p-hydroxyphenylacetate 32.4 g of α-chloro-N-methylacetamide, 45.6 g of p-hydroxyphenylacetic acid and 50 ml of triethylamine was added to 300 ml of acetonitrile, and the mixture was refluxed for 7 hrs. After the completion of the reaction, the reaction mixture was then concentrated under reduced pressure. The resulting residue was subjected to column chromatography using silica gel and the column was eluted with (1) benzene, (2) benzene: ethylacetate= 2:3 (v/v) and (3) ethyl acetate in the recited order. From the thus obtained fraction the desired compound (N-methylcarbamoylmethyl-p-hydroxyphenylacetate) in an amount of 43 g was obtained in an oily form.

Elemental Analysis: Calcd. for $C_{11}H_{13}O_4N$ (%): C 59.18, H 5.87, N 6.28 Found (%): C 59.35, H, 5.68, N 6.43

EXAMPLE 9

Carbamoylmethyl-p-(p-Guanidinobenzoyloxy)Benzoate Mesylate 60 g of thionyl chloride was added to 2.8 g of p-guanidinobenzoic acid, and the mixture was refluxed about 30 minutes to form an acid chloride hydrochloride. The product was added to a solution of 2.9 g of carbamoylmethyl-p-hydroxybenzoate prepared as described in Example 1 in 20 ml of pyridine at room temperature followed by stirring for 1 hour. To the reaction mixture there was added a saturated aqueous solution of sodium bicarbonate to form crystals, which were then filtered and washed with water and acetone. The crystals were suspended in a small amount of water, and the suspension was rendered weakly acidic (pH 3) by adding methanesulfonic acid, while stirring, to form a solution. The resulting solution was allowed to stand while cool to precipitate crystals, which were then filtered and recrystallized from ethanol to obtain 2.1 g of the above-titled compound having a melting point of 167°–170° C.

Elemental Analysis: Calcd. for $C_{17}H_{16}N_4O_5 \cdot CH_3SO_3H$ (%): C 47.76, H 4.45, N 12.38, S 7.09. Found (%): C 47.58, H 4.31, N 12.54, S 6.88.

Thin Layer Chromatography (TLC) [$CH_3COOC_2H_5:CH_3COOH:H_2O=$ 3:1:1 by volume (hereinafter the same)]: Rf = 0.74

EXAMPLE 10

N-Methylcarbamoylmethyl-p-(p-Guanidinobenzoyloxy)-Benzoate Mesylate 7.7 g of N-methylcarbamoylmethyl-p-hydroxybenzoate prepared as described in Example 3 was dissolved in 60 ml of pyridine. To the solution was added an acid chloride.hydrochloride obtained from 7.0 g of p-guanidinobenzoic acid and thionyl chloride, and the mixture was stirred at room temperature for 2 hours. The precipitated crystals were filtered and added to an aqueous solution of sodium bicarbonate to form crystals, which were then filtered and suspended in ethanol. The suspension was rendered acidic with methanesulfonic acid followed by cooling to 5° C to crystallize the product. Recrystallization of the product from ethanol gave 7.0 g of the above-titled compound having a melting point of 205°–210° C.

Elemental Analysis: Calcd. for $C_{18}H_{18}N_4O_5 \cdot CH_3SO_3H$ (%): C 48.92, H 4.75, N 12.01, S 6.87. Found (%): C 48.73, H 4.58, N 12.25, S 7.11. TLC: Rf = 0.63

EXAMPLE 11

N,N-Dimethylcarbamoylmethyl-p-(p-Guanidinobenzoyloxy)-Benzoate Mesylate 4.4 g of N,N-dimethylcarbamoylmethyl-p-hydroxybenzoate prepared as described in Example 2 was dissolved in 30 ml of pyridine, and an acid chloride hydrochloride obtained from 3.6 g of p-guanidinolbenzoic acid was added thereto. The resulting mixture was stirred at room temperature for 2 hours. The precipitated crystals were filtered and added to an aqueous solution of sodium bicarbonate followed by stirring for a short time. The precipitated crystals were filtered and suspended in methanol. The suspension was rendered acidic (pH 3) with methanesulfonic acid and filtered. Ethanol was added to the filtrate to precipitate crystals, which were filtered and then purified by recrystallization from methanol-diethyl ether (1:10 by volume) to obtain 2.0 g of the above-titled compound having a melting point of 200°–203° C.

Elemental Analysis: Calcd. for $C_{19}H_{20}N_4O_5 \cdot CH_3SO_3H$ (%): C 49.99, H. 5.03, N 11.66, S 6.67. Found (%): C 50.24, H 5.19, N 11.46, S 6.41. TLC: Rf = 0.61

EXAMPLE 12

N,N-Di-n-Propylcarbamoylmethyl-p-(p-Guanidinobenzoyloxy)Benzoate Tosylate 6.5 g of N,N-di-n-propylcarbamoylmethyl-p-hydroxybenzoate was reacted with an acid chloride prepared from 4.2 g of p-guanidinobenzoic acid in pyridine. The resulting crystals were added to an aqueous solution of sodium bicarbonate to form a carbonate of the product. The thus formed crystals were added to toluenesulfonic acid in methanol (final pH 3) to form a toluenesulfonate, followed by recrystallization from methanol to obtain 5.7 g of the above-titled compound having a melting point of 153°–155° C.

Elemental Analysis: Calcd. for $C_{23}H_{28}N_4O_5 \cdot CH_3C_6H_4SO_3H$ (%): C 58.81, H 5.88, N 9.14, S 5.23. Found (%): C 59.04, H 5.61, N 9.37, S 5.45. TLC: Rf = 0.64

EXAMPLE 13

N,N-Dimethylcarbamoylmethyl-p-(p-Guanidinobenzoyloxy)Phenylacetate Mesylate 7 g of N,N-dimethylcarbamoylmethyl-p-hydroxyphenylacetate prepared as described in Example 5 was dissolved in 40 ml of pyridine, and an acid chloride prepared from 5.6 g of p-guandinobenzoic acid was added to the solution. The resulting mixture was stirred at room temperature for 2 hours, and an excess of an aqueous solution of sodium bicarbonate was added thereto to precipitate crystals of the desired product in the form of the carbonate. The thus obtained crystals were filtered, washed with water and acetone and then suspended in methanol. The suspension was rendered weakly acidic with methanesulfonic acid and then warmed to about 50° C followed by filtration. Diethyl ether was added to the filtrate to obtain 4.9 g of the above-titled compound having a melting point of 150°–155° C.

Elemental Analysis: Calcd. for $C_{20}H_{22}N_4O_5 \cdot CH_3SO_3H$ (%): C 51.00, H 5.23, N 11.33, S 6.48. Found (%): C 51.21, H 5.06, N 11.49, S 6.71. TLC: Rf = 0.60

EXAMPLE 14

N,N-Dimethylcarbamoylmethyl-p-(p-Guanidinobenzoyloxy)Cinnamate Mesylate 5 g of N,N-dimethylcarbamoylmethyl-p-hydroxycinnamate prepared as described in Example 6 was dissolved in 50 ml of pyridine, and an acid chloride prepared from 4 g of p-guanidinobenzoic acid was added to the solution. The mixture was stirred at room temperature for 2 hours, and an excess of an aqueous solution of sodium bicarbonate was added to the reaction mixture to precipitate crystals in the form of the carbonate of the product. The crystals were filtered, washed with water and acetone and then suspended in methanol. The suspension was made weakly acidic (pH 3) with methanesulfonic acid, warmed to about 50° C and filtered. Diethyl ether was added to the filtrate to obtain 5.1 g of the above-titled compound having a melting point of 155° C.

Elemental Analysis: Calcd. for $C_{21}H_{22}N_4O_5 \cdot CH_3SO_3H$ (%): C 52.16, H 5.17, N 11.06, S 6.33. Found (%): C 52.41, H 5.02, N 11.23, S 6.14. TLC: Rf = 0.61

EXAMPLE 15

N,N-Dimethylcarbamoylmethyl-p-(p-Guanidinobenzoyloxy)Phenylpropionate Mesylate 5 g of N,N-dimethylcarbamoylmethyl-p-hydroxyphenylpropionate prepared as described in Example 7 was dissolved in 50 ml of pyridine, and an acid chloride prepared from 4 g of p-guanidinobenzoic acid was added thereto. The resulting mixture was stirred at room temperature for 2 hours, and an excess of an aqueous solution of sodium bicarbonate was added to the reaction mixture to precipitate crystals, which were then filtered, washed with water and acetone and suspended in methanol. The suspension was made weakly acidic (pH 3) with methanesulfonic acid, warmed to about 50° C and then filtered. Diethyl ether was added to the filtrate to obtain 6.3 g of the above-titled compound having a melting point of 162°–165° C.

Elemental Analysis: Calcd. for $C_{21}H_{24}N_4O_5 \cdot CH_3SO_3H$ (%): C 51.96, H 5.55, N 11.02, S 6.30. Found (%): C 51.77, H 5.38, N 11.25, S 6.41. TLC: Rf = 0.53

EXAMPLE 16

N-Methylcarbamoylmethyl-p-(p-guanidinobenzoyloxy)phenylacetate Mesylate 10 g of N-methylcarbamoylmethyl-p-hydroxyphenylacetate was dissolved in 60 ml of pyridine, and acid chloride obtained from 8 g of p-guanidinobenzoic acid was added to the solution. The resulting mixture was stirred at room temperature for 3 hours, and an excess of diethyl ether was added to the reaction mixture to cause precipitation. The diethyl ether fraction containing pyridine was decanted, and 100 ml of water was added to the residue to cool it and to precipitate crystals, which were then filtered and washed with water. The thus obtained crystals were dissolved in about 100 ml of water and the solution filtered in the presence of activated carbon. An excess amount of a saturated aqueous solution of sodium bicarbonate was added to the solution to precipitate crystals, which were filtered out, washed with water and acetone and dried. The dried crystals were suspended in 100 ml of methanol, and the suspension was rendered acidic (pH 3) with methanesulfonic acid to dissolve the crystals, the obtained solution then being filtered. Diethyl ether was gradually added to the filtrate to precipitate crystals, which were then filtered, washed with diethyl ether and dried. For purification, the crystals were redissolved in about 50 ml of methanol and diethyl ether was gradually added to the solution. The resulting precipitated crystals were filtered to obtain 4.3 g of N-methylcarbamoylmethyl-p-(p-guanidinobenzoyloxy)phenylacetate mesylate.

Elemental Analysis: Calcd. for $C_{19}H_{20}N_4O_5 \cdot CH_3SO_3H$ (%): C 49.99, H 5.03, N 11.66, S 6.67. Found (%): C 50.21, H 5.18, N 11.44, S 6.39. TLC: Rf = 0.46.

While the invention has been described in detail with reference to specific embodiments thereof, it will be apparent to one skilled in the art that various changes and modifications can be made therein without departing from the spirit and the scope thereof.

What is claimed is:

1. N-substituted guanidinobenzoic acid derivatives represented by the formula

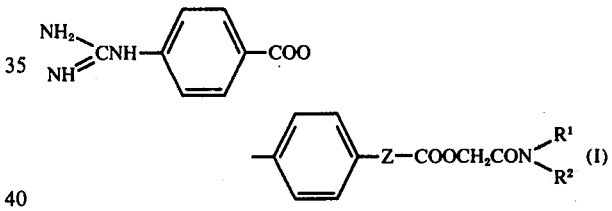

wherein $R^1$ and $R^2$ may be the same or different and each represents a hydrogen atom or a lower alkyl group having 1 to 3 carbon atoms, and Z represents a methylene group, an ethylene group, or a vinylene group, and pharmaceutically acceptable acid addition salts thereof.

2. The guanidinobenzoic acid derivatives according to claim 1, wherein said acid addition salts are salts with an acid selected from the group consisting of hydrochloric, sulfuric, phosphoric, hydrobromic, nitric, acetic, lactic, oxalic, maleic, fumaric, malic, tartaric, citric, ascorbic, benzenesulfonic, toluenesulfonic and methanesulfonic.

3. N,N-dimethyl-carbamoylmethyl-p-(p-guanidinobenzoyloxy)-phenylacetate and acid addition salts thereof according to claim 2.

4. N,N-dimethyl-carbamoylmethyl-p-(p-guanidinobenzoyloxy)-cinnamate and acid addition salts thereof according to claim 2.

5. N,N-dimethyl-carbamoylmethyl-p-(p-guanidinobenzoyloxy)-phenylpropionate and acid addition salts thereof according to claim 2.

6. N-methylcarbamoylmethyl-p-(paraguanidinobenzoyloxy)-phenylacetate and acid addition salts thereof according to claim 2.

* * * * *